US00PP09032P

United States Patent [19]

Twomey

[11] Patent Number: Plant 9,032

[45] Date of Patent: Jan. 3, 1995

[54] FLORIBUNDA ROSE PLANT NAMED TWORIGHT

[75] Inventor: Jerry Twomey, Aptos, Calif.

[73] Assignee: DeVor Nurseries, Inc., Watsonville, Calif.

[21] Appl. No.: 86,430

[22] Filed: Jun. 30, 1993 (Under 37 CFR 1.47)

[51] Int. Cl.[6] ..... A01H 5/00

[52] U.S. Cl. ..... Plt./28

[58] Field of Search ..... Plt. 22, 28

[56] References Cited

U.S. PATENT DOCUMENT

PP3546 5/1974 Meilland ..... Plt./28

*Primary Examiner*—Howard J. Locker

*Attorney, Agent, or Firm*—Christie, Parker & Hale

[57] ABSTRACT

A new floribunda rose plant producing bright red flowers.

1 Drawing Sheet

SUMMARY OF THE INVENTION

The present invention relates to a new and distinct variety of rose plant of the floribunda rose class which was originated by my crossing as seed parent an unnamed and unpatented seedling of my creation and as pollen parent the variety known as 'Evening Star' (U.S. Plant Pat. No. 3,432). The varietal denomination of this new rose is 'Tworight'.

Among the novel characteristics possessed by this new variety which distinguish it from its parents and all other varieties of which I am aware are its attractive, bright red flowers borne on a plant resistant to mildew and blackspot.

Asexual reproduction by budding as performed in Watsonville, Calif. shows that the foregoing and other distinguishing characteristics come true to form and are established and transmitted through succeeding propagations.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage:

*Seed parent.*—Seedling.

*Pollen parent.*—'Evening Star'.

Class: Floribunda.

The following is a detailed description of specimens of the new variety, grown outdoors in Watsonville, Calif. in September with color terminology in accordance with the Royal Horticultural Society Colour Chart (RHSCC). The terminology used in color descriptions herein refers to plate numbers in the aforementioned color chart. Phenotypic expression may vary with environmental and cultural conditions.

FLOWER

Blooming habit: Recurrent.

A. Bud:

(1) *Size.*—Small.

(2) *Form.*—Globular, slightly pointed.

(3) *Color.*—As sepals divide, bud color is near 46A.

(4) *Sepals.*—Sepals spread after parting and then reflex; approximately 2 cm long. Color: Near 147D at base, becoming near 147B; tiny white hairs on inside of sepals.

(5) *Peduncle.*—Length: About 5.5 to 6.5 cm. Aspect: Straight with small prickles. Strength: Erect. Color: Near 176B to near 146B.

(6) *Bracts.*—1 to 2, near 146A inside with near 187A along edges; broadly elliptical with acute tip, about 5 to 6 cm below calyx.

B. Bloom:

(1) *Size.*—Average size when fully expanded — about 8 to 8.5 cm.

(2) *Borne.*—Several together in sprays of 3 to 4 blooms.

(3) *Form.*—Imbricated, with petals becoming slightly rolled back at maturity.

(4) *Petalage.*—Number of petals under normal conditions — about 45 to 47; 3 to 5 petaloids.

(5) *Color.*—When ⅓ to ½ open, the top surface of the outer petals is near 45B; near 55A toward base with near 1C at base. The undersurface of the outer petals is near 53B; near 55A toward base with near 1C at base. When ⅓ to ½ open, the top surface of the inner petals is near 45B; near 55A toward base with near 38D at base. The undersurface of the inner petals is near 53B; near 55A toward base with near 36C at base, and the base of petals at point of attachment is near 1B. When fully open, the top surface of the inner petals is near 44B; near 55A toward base with near 157B at base. The undersurface of the inner petals is near 52A; near 55A toward base with near 157B at base, the base of petals at point of attachment is near 157B, and the general tonality at a distance is orange-red. As bloom ages, the color changes from a reddish tone to a more orange-red coloration. The petal top surface is near 44B, the petal undersurface is near 53A and the general tonality at a distance is orange-red.

C. Petals:
(1) *Texture.*—Medium, smooth.
(2) *Appearance.*—Inside and outside slightly leathery.
(3) *Form.*—Slightly ruffled.
(4) *Arrangement.*—Regularly arranged, imbricated.
(5) *Fragrance.*—Moderate, sweet.
(6) *Lasting quality.*—Average for floribunda on plant and as cut flower; petals drop cleanly.

REPRODUCTIVE ORGANS

A. Stamens:
(1) *Arrangement.*—Introrse, near 22A.
(2) *Anthers.*—Color — near 22A.
(3) *Filaments (threads).*—Color — near 157D at tip with near 51C at base.
(4) *Pollen.*—Color — near 22A.

B. Pistils:
(1) *Styles.*—Bunched, even, medium length.
(2) *Stigmas.*—Color — near 163D.

C. Characteristics of hips:
(1) *Shape.*—Obovate, with depressed top; seeds do not protrude.
(2) *Size.*—About 2 cm by 2 cm.
(3) *Color at maturity.*—near 28A.

PLANT

A. Form: Upright, bushy.
B. Growth: Vigorous; height attained about 122 to 127 cm at first year.
C. Foliage: Compound 3 to 7 leaflets.
(1) *Size.*—Medium.
(2) *Quantity.*—Abundant.
(3) *Color.*—New foliage, upper side — near 147A, underside — near 147B; Old foliage, upper side — near 146A, underside — near 148B.
(4) *Shape.*—Oblong.
(5) *Texture.*—Leathery; semiglossy top, dull underside.
(6) *Edge.*—Serrate.
(7) *Serration.*—Denticulate.
(8) *Leaf stem.*—Color — medium green.
(9) *Stipules.*—Hairy, medium length, hirsute, slender.
(10) *Petiole.*—Top — near 176A; bottom — near 146D.
(11) *Rachis.*—Small prickles.
(12) *Auricle.*—Slender with small hairs.
(13) *Resistance to disease.*—Very resistant to blackspot and mildew, good resistance to rust.

D. Wood
(1) *New wood.*—Color — near 146A. Bark — smooth.
(2) *Old wood.*—Color — near 146B. Bark — smooth.

E. Flower stem: About 50 to 53 cm from last flower cut.
F. Thorns:
*Quantity (main stalk).*—Profuse.
*On laterals from stalk.*—Few.
*Form.*—Thin, slightly turned downward.
*Length.*—Medium.
*Color.*—Near 178A.
*Position.*—Irregular.
*Prickles.*—Profuse.
F. Winter hardiness: Wintered well in California.

I claim:
1. A new and distinct variety of rose plant of the floribunda rose class, substantially as shown and described.

* * * * *

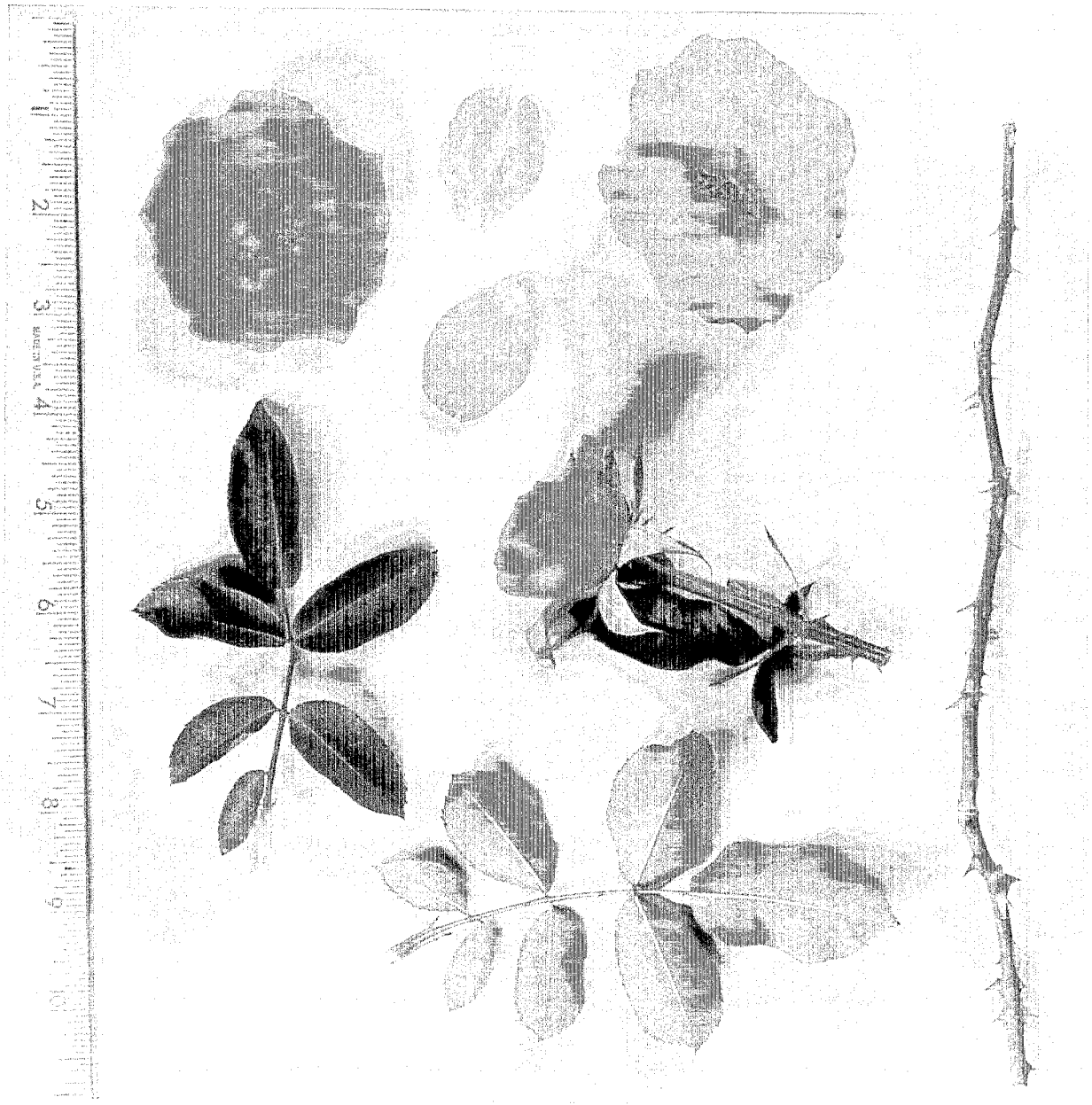
1
2
3
4
5
6
7
8
9
10
centimeters